United States Patent [19]
Kaan et al.

[11] Patent Number: 5,972,948
[45] Date of Patent: *Oct. 26, 1999

[54] METHOD OF INHIBITING HYPERGLYCEMIA AND PHARMACEUTICAL COMPOSITION FOR USE THEREIN

[75] Inventors: Elbert Kaan, Grossburgwedel; Dieter Ziegler, Hemmingen; Reinhard Brueckner, Hannover, all of Germany

[73] Assignee: Solvay Pharmaceuticals GmbH, Hannover, Germany

[ * ] Notice: This patent is subject to a terminal disclaimer.

[21] Appl. No.: 08/917,169

[22] Filed: Aug. 25, 1997

Related U.S. Application Data

[63] Continuation-in-part of application No. 08/492,656, Jun. 20, 1995, Pat. No. 5,712,283.

[30] Foreign Application Priority Data

Jul. 1, 1994 [DE] Germany .............................. 44 23 177

[51] Int. Cl.⁶ .................................................. A01N 43/50
[52] U.S. Cl. .............................................................. 514/269
[58] Field of Search ............................................. 514/269

[56] References Cited

U.S. PATENT DOCUMENTS

| | | |
|---|---|---|
| 4,323,570 | 4/1982 | Stenzel et al. . |
| 5,296,498 | 3/1994 | Malen et al. . |
| 5,494,934 | 2/1996 | Malen et al. . |
| 5,574,059 | 11/1996 | Regunathan et al. ................... 514/397 |
| 5,795,909 | 8/1998 | Shashoua et al. ...................... 514/449 |

OTHER PUBLICATIONS

Muller et al., "Steady State Investigation of Possible Pharmacokinetic Interactions of Moxonodine and Glibenclamide", *European Journal of Metabolism and Pharmacokinetics*, 1993, vol. 18, No. 3, pp. 277–283.

Schwarz et al., "Langzeiterfahrungen mit Monoxnoidin, einem neuen Antihypertensivum", *Fortschr. Med.* 108 (1990), No. 32, pp. 616–620.

Rupp et al., "Modification of Myosin Isozymes and SR $Ca^{2+}$–pump ATPase of the Diabetic Rat . . . ", *Molecular and Cellular Biology*, 132:69–80 (1994).

Michel et al., "From $\alpha_2$–Adrenoceptors to Imidazoline Receptors: Putative Progress fro Cardiovascular Therapy", *Journal of Cardiovascular Pharmacology*, 20 (Suppl. 4): S24–S30 (1992).

Rupp et al., *Therapiewoche*, vol. 43, No. 32/33, pp. 1686–93 (1993).

Dotzer et al., *Z. Allg. Med.*, 68:760–763 (1992).

Trieb et al., "Wirksamkeit und Vertraeglichkeit des Imidazol–Receptor–Agonisten", *Therapiestudien*, 1994, 45: 440–45.

*Primary Examiner*—Jeffrey Mullis
*Attorney, Agent, or Firm*—Evenson, McKeown, Edwards & Lenahan, P.L.L.C.

[57] ABSTRACT

A method of using moxonidine or a physiologically acceptable acid addition salt thereof for the treatment and/or prophylaxis of glucose metabolism disorders such as insulin resistance and/or glucose intolerance, and pharmaceutical compositions for use therein.

6 Claims, 2 Drawing Sheets

Fig. 1 Oral Glucose Tolerance Test: Effect of Moxonidine
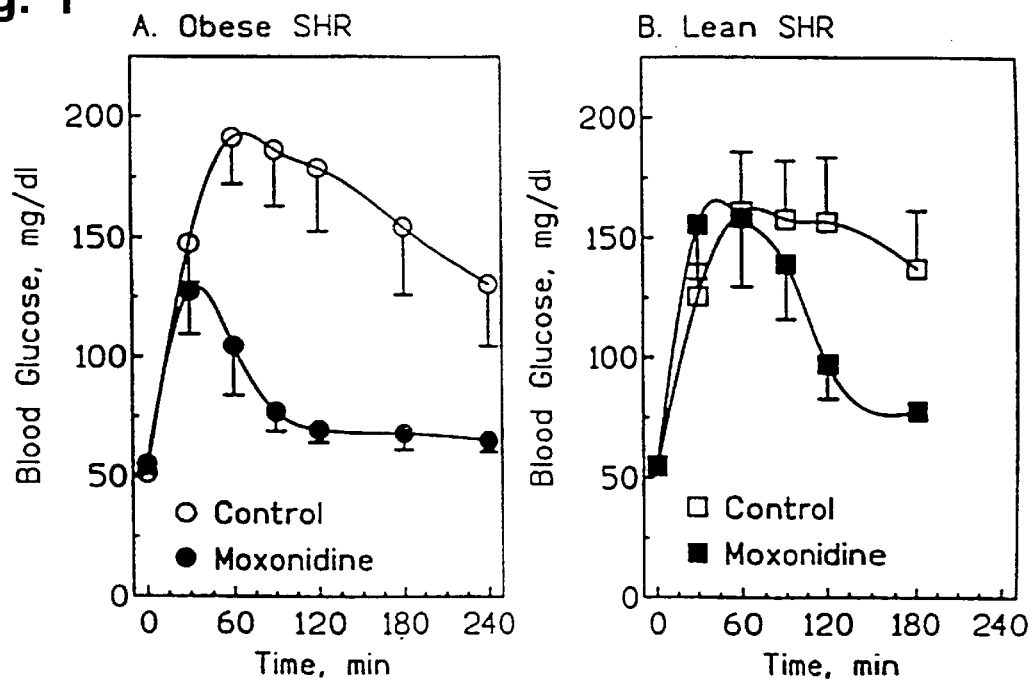
Fig. 2
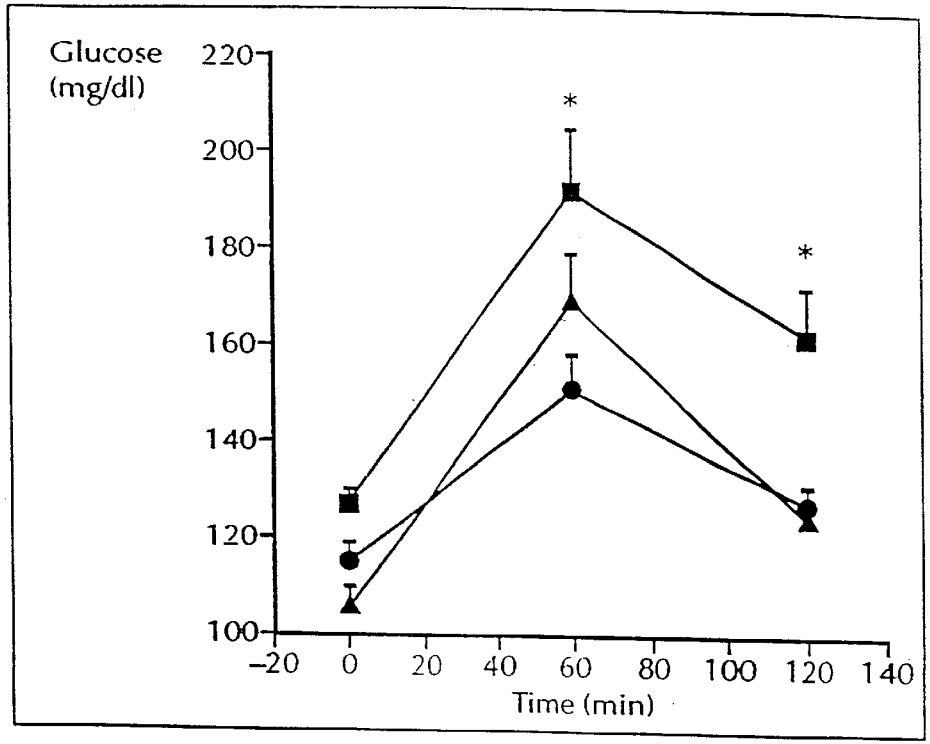
● Control rats
■ Fructose-fed rats
▲ Fructose-fed + moxonidine
* $P < 0.05$ Fructose-fed rats verses Control rats

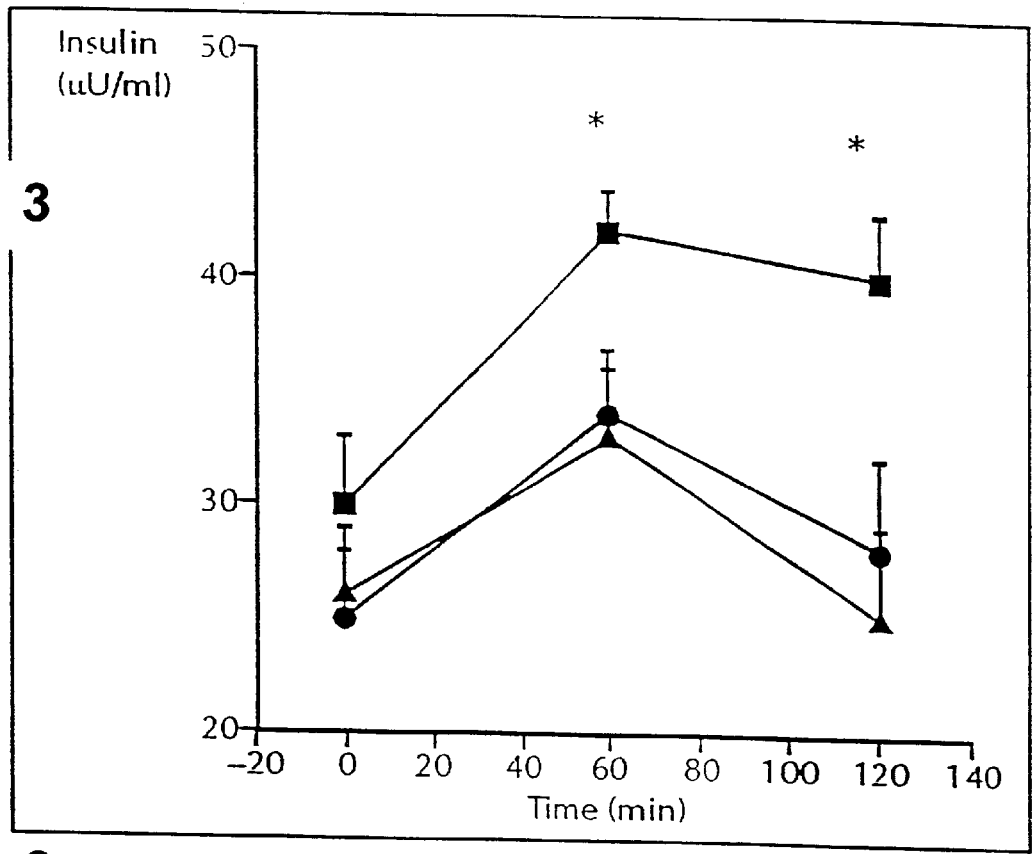

METHOD OF INHIBITING HYPERGLYCEMIA AND PHARMACEUTICAL COMPOSITION FOR USE THEREIN

CROSS REFERENCE TO RELATED APPLICATION

This application is a continuation-in-part of our application Ser. No. 08/492,656, filed Jun. 20, 1995, now U.S. Pat. No. 5,712,283.

BACKGROUND OF THE INVENTION

The present invention relates to the use of 4-chloro-5-[(4,5-dihydro-1H-imidazol-2-yl)amino]-6-methoxy-2-methylpyrimidine (=moxonidine) and its physiologically acceptable acid addition salts for the treatment and/or prophylaxis of glucose metabolism disorders, and for the production of medicaments suitable for this treatment.

SUMMARY OF THE INVENTION

It is the object of the invention to provide a method of inhibiting hyperglycemia.

Another object is to provide novel pharmaceutical preparations for the treatment of metabolic disorders which can lead to hyperglycemias.

In accordance with a first aspect of the invention, the object is achieved by providing a method of inhibiting hyperglycemia in a mammal by administering to said mammal an effective hyperglycemia inhibiting amount of a compound corresponding to formula I

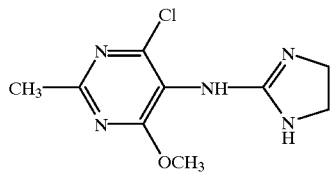

or a physiologically acceptable acid addition salt thereof.

In accordance with a further aspect of the invention, 4-chloro-5-[(4,5-dihydro-1H-imidazol-2-yl)amino]-6-methoxy-2-methylpyrimidine of formula I

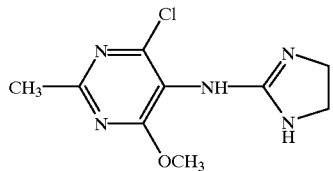

and its physiologically acceptable acid addition salts are used for the production of pharmaceutical preparations for this treatment.

Suitable physiologically acceptable acid addition salts of moxonidine include salts with inorganic acids, for example hydrohalic acids, or with organic acids, for example lower aliphatic monocarboxylic or dicarboxylic acids such as acetic acid, fumaric acid or tartaric acid or aromatic carboxylic acids such as e.g. salicylic acid.

The compounds employed according to the invention for the treatment of glucose metabolism disorders fall under the scope of 5-[(2-imidazolin-2-yl)amino]pyrimidine derivatives having hypotensive properties described in German Offenlegungsschrift No. 28 49 537, and are disclosed in this Patent Application. Moxonidine-containing pharmaceutical preparations are obtainable commercially as antihypertensives under the trade name Physiotens™ and are employed medicinally as an antihypertensive. The compounds can be prepared in a known manner in accordance with, or analogously to, the process described in the aforementioned German Offenlegungsschrift.

BRIEF DESCRIPTION OF THE DRAWINGS

FIGS. 1a and 1b are graphs of the results of the effect of moxonidine administration on oral glucose tolerance in obese spontaneously hypertensive rats and in lean spontaneously hypertensive rats, respectively.

FIG. 2 is a graph showing the effect of moxonidine administration on glucose tolerance in fructose fed insulin resistant rats and normal control rats.

FIG. 3 is a graph showing the effect of moxonidine administration on blood insulin levels in fructose fed insulin resistant rats and normal control rats.

DETAILED DESCRIPTION OF PREFERRED EMBODIMENTS

It has now surprisingly been found that moxonidine and its physiologically acceptable acid addition salts have an anti-hyperglycemic action in humans and larger mammals and are suitable for the treatment of disorders of the glucose metabolism of varying origin which are associated with hyperglycemia, for example the occurrence of raised plasma glucose values as a result of increased glucose release and/or decreased metabolic glucose utilization, which can be connected with raised blood pressure, insulin resistance, glucose intolerance, type II diabetes and/or obesity.

For the treatment according to the invention of hyperglycemic conditions, moxonidine and its physiologically acceptable acid addition salts can be administered orally, intravenously or even transdermally in customary pharmaceutical preparations.

Anti-hyperglycemically active amounts of the compounds according to the invention can thus be contained in solid or liquid pharmaceutical preparations together with customary pharmaceutical auxiliaries and/or excipients. Examples of solid preparations which may be mentioned include orally administrable preparations such as tablets, coated tablets, capsules, powders or granules or even suppositories. These solid preparations can contain conventional inorganic and/or organic pharmaceutical excipients such as e.g. lactose, talc or starch in addition to conventional pharmaceutical adjuvants, for example lubricants or tablet disintegrants. Liquid preparations such as solutions, suspensions or emulsions of the active compounds may contain the customary diluents such as water, oils and/or suspending agents such as polyethylene glycols and the like. Further adjuvants can additionally be added, such as e.g. preservatives, flavor correctants and the like.

The active compounds can be mixed and formulated with the pharmaceutical adjuvants and/or excipients in a known manner. In order to prepare solid pharmaceutical forms, for example, the active compounds can be mixed and granulated in wet or dry form with the adjuvants and/or excipients in a customary manner. The granules or powder can then be filled directly into capsules or compressed to give tablet cores in a conventional manner. If desired, these can be sugar coated in a known manner.

The anti-hyperglycemic action of moxonidine was demonstrated in animal experiments and in clinical studies on patients with differing degrees of hyperglycemia.

Test 1

A double-blind study was carried out with a total of 228 patients over a period of 6 weeks. The patients were randomly divided into 4 groups. All patients each had to take one tablet twice daily. In a preliminary test phase of 4 weeks, all patients received placebo tablets. In the actual test phase one control group (=group K) of patients received placebo tablets, a first test group (=group 1) received tablets containing 0.1 mg of moxonidine per tablet, a second test group (=group 2) received tablets containing 0.2 mg of moxonidine per tablet and a third test group (=group 3) received tablets containing 0.4 mg of moxonidine per tablet. Blood samples were taken from each patient in the fasting state on the day before the start of the test phase and after 6 weeks on the last day of the test phase. The plasma blood sugar values in these samples were measured in mg of glucose per deciliter.

To assess the results of measurement, a further subdivision into two subgroups each was performed for each of the 4 groups:

A) Subjects having normal starting plasma glucose values in the range of ≦115 mg/dl.

B) Subjects having pathologically elevated starting plasma glucose values of >115 mg/dl. This subgroup includes patients with slightly elevated starting plasma glucose values in the range from 115 to 139 mg/dl and patients with distinctly elevated starting plasma glucose values in the diabetes range (≧140 mg/dl). The results of measurement of these sub-subgroups B1) of diabetes patients were again separately assessed.

The following table indicates for all subgroups the calculated statistical mean values (±standard error) of the plasma blood sugar determinations.

TABLE

Change in plasma glucose values.

| Medication | Patient group | Number of patients | Plasma glucose values in mg/dl (mean values ± standard error) | |
|---|---|---|---|---|
| | | | starting value | final value |
| Placebo | KA | 49 | 94 (±1) | 93 (±2) |
| | KB | 9 | 134 (±5) | 129 (±6) |
| | KB1 | 1 | 172 | 174 |
| 0.1 mg of moxonidine 2 × daily | 1A | 52 | 95 (±1) | 93 (±2) |
| | 1B | 7 | 131 (±8) | 117 (±4) |
| | 1B1 | 1 | 183 | 103 |
| 0.2 mg of moxonidine 2 × daily | 2A | 45 | 93 (±2) | 94 (±2) |
| | 2B | 10 | 170 (±17) | 134 (±10) |
| | 2B1 | 6 | 198 (±21) | 144 (±12) |
| 0.4 mg of moxonidine 2 × daily | 3A | 46 | 92 (±2) | 91 (±2) |
| | 3B | 10 | 130 (±5) | 120 (±10) |
| | 3B1 | 2 | 158 (±7) | 139 (±28) |

From the foregoing table it is evident that during the test phase in all patients treated only with placebo virtually no change in the blood sugar values occurred independently of the starting plasma glucose value. In the patients treated with various doses of moxonidine it was found that in patients with normal starting plasma glucose values likewise virtually no change in the plasma glucose values occurred. In patients with elevated starting plasma glucose values, however, a distinct decrease in these plasma glucose values occurred as a result of the moxonidine treatment, this reduction in the plasma glucose values being greater the higher the starting plasma glucose values.

The foregoing experimental results show that moxonidine exerts an anti-hyperglycemic action and causes the reduction of raised blood sugar values without, however, adversely affecting normal blood sugar values. These experimental results are also to be judged as an index for the fact that moxonidine has a favorable effect on insulin resistance. Moxonidine and its acid addition salts are therefore suitable for the treatment of such glucose metabolism disturbances.

Test 2

In the course of an investigation of the relationship between sympathetic nervous system activity, diet and hypertension in spontaneously hypertensive rats, the anti-hypertensive drug moxonidine was administered to the animals. The test animals were obese spontaneously hypertensive rats (SHROB), also known as Koletsky rats. The SHROB rat is an animal model with multiple metabolic abnormalities resembling human syndrome X, a condition which consists of insulin resistance as a primary defect associated with compensatory hyperinsulinemia and impaired glucose tolerance, as well as other conditions [See Reaven, *Ann. Rev. Med.*, Vol. 44, pages 121–31 (1993)]. Lean spontaneously hypertensive rats (SHR rats) also were tested.

Both SHROB and SHR rats were treated with moxonidine at a dose of 8 mg/kg/day. The rats received moxonidine in their drinking water for 90 days. The concentration of moxonidine in each rat's water bottle was adjusted weekly in accordance with changes in fluid consumption and body weight. Saccharin (0.1%) was added to the moxonidine solution to maintain palatability. Glucose tolerance and blood insulin levels were tested and compared to animals which received no moxonidine.

Glucose tolerance was tested by fasting animals for 18 hours and then administering 12 g of glucose per kg of body weight by gavage. Blood (0.2 ml) was obtained from a cut on the tail at 30, 60, 90, 120, 180 and 240 minutes, and glucose was measured by colorimetric glucose oxidase assay (One-Touch, Life-scan, Milpitas, Calif.). The results are shown graphically in FIG. 1*a* for obese test animals and in FIG. 1*b* for lean test animals.

Fasting blood glucose levels were in the physiological range and did not differ between SHROB and lean SHR, and were not affected by moxonidine. Blood glucose levels following oral challenge were not significantly different between SHROB and SHR. Moxonidine improved impaired glucose tolerance in both SHROB and SHR. In SHROB, blood glucose levels were lower in the moxonidine-treated group from 60 minutes onwards. In lean SHR, blood glucose levels were reduced at 120 and 180 minutes.

Blood insulin levels were determined by insulin radioimmunoassay. Fasting blood samples (0.5 ml) for insulin measurement were immediately centrifuged, and plasma samples were stored at −20° C. until assayed. A radioimmunoassay kit (Linco Research, St. Charles, Mo.) was used with rat insulin standard and antibodies directed against rat insulin. Assays were conducted in duplicate, and the intra-assay coefficient of variation was less than 5%. The results are shown in the following table:

| | SHROB | | Lean SHR | |
|---|---|---|---|---|
| | Control (n = 14) | Moxonidine (n = 5) | Control (n = 5) | Moxonidine (n = 6) |
| insulin (ng/ml) | 20 + 3 | 7 + 1 | 0.67 + 0.08 | 0.96 + 0.16 |

The test results show that moxonidine partially reversed hyperinsulinemia in SHROB by producing a significant lowering of blood insulin levels.

The foregoing test results demonstrate that moxonidine ameliorates insulin resistance and improves glucose tolerance in SHROB.

Test 3

The influence of moxonidine on glucose tolerance in vivo was determined in healthy control rats, in rats receiving a high fructose diet for six weeks to induce insulin resistance, hyperinsulinemia and hypertension, and in rats receiving a high fructose diet plus moxonidine (1.5 mg/kg body weight daily). Male Wistar rats (Harlan-Winkelmann, Borchen, Germany) weighing 250–280 g were housed in an environmentally controlled room with a 12 hour light/dark cycle and were allowed free access to food and water.

After a six day acclimation period, the rats were divided into three groups and fed ad libitum one of the following diets for six weeks: (1) normal rat chow (Sniff, Soest, Germany), given to rats that served as controls; (2) high fructose diet, given for induction of insulin resistance and hyperinsulinemia; and (3) high fructose diet plus moxonidine. The high fructose diet provided 60% of total calories as fructose. Fructose in the diet had no influence on the gain of body weight and the food intake. Moxonidine was freshly dissolved daily and applied in the drinking water. The concentration was adjusted daily to ensure a dose of 1.5 mg/kg body weight per day. The results of blood glucose measurements and blood insulin measurements are shown in the following table.

|  | Chow fed | Fructose fed | Fructose fed + moxonidine |
|---|---|---|---|
| Fasting plasma glucose (mmole/l) | 4.5 + 0.3 | 4.7 + 0.2 | 4.4 + 0.3 |
| Fasting plasma insulin (pmole/l) | 2.5 + 0.5 | 5.5 + 0.7 | 2.1 + 0.3 |

As can be seen from the table, after the six week feeding period, the fasting plasma glucose levels were not significantly different among the three groups. The fasting plasma insulin levels were, however, nearly doubled in the fructose-fed group compared with the controls, but were unchanged in the moxonidine-treated rats.

To determine the glucose tolerance the rats each received 2 g glucose dissolved in physiological NaCl solution. For the measurement of plasma glucose levels, blood was taken from the tail vein 0, 30, 60, 90, 120 minutes and 24 hours after glucose loading. Plasma glucose was measured by the glucose oxidase method (Beckman Glucose Analyzer, Munich, Germany). Results at 0, 60 and 120 minutes after glucose loading are shown in FIG. 2.

In control rats loading with glucose lead to a rapid increase in plasma glucose levels reaching a maximum after about 30 to 60 minutes. Two hours after loading the glucose levels were already at basal level and were no different from the initial values before glucose loading. In fructose-fed rats the maximum of plasma glucose after glucose loading was significantly increased compared with the control rats (190 verses 150 mg/dl) and the decline in glucose levels was markedly delayed. Treatment with moxonidine prevented the changes in glucose tolerance induced by fructose feeding and resulted in blood glucose measurement levels similar to those of the control rats.

To determine the insulin level, the rats were anesthetized, and blood samples were taken from the heart at predetermined time intervals. Insulin levels were measured by standard methods. Results for blood samples taken 0, 60 and 120 minutes after glucose loading are shown in FIG. 3.

Plasma insulin levels among the groups of anesthetized rats were not significantly different before glucose loading, but were increased in the fructose-fed rats and remained elevated during the observation period indicating a hyperinsulinemic and insulin-resistant state. The plasma insulin levels measured in the moxonidine-treated rats were not significantly different from controls.

The data indicates that rats fed the high fructose diet suffered impaired glucose utilization accompanied by an increase in plasma insulin. This means that the increased glucose levels are not due to diminished secretion of insulin, but result instead from insulin resistance. To compensate for the reduction in insulin sensitivity and the increasing blood glucose levels, the secretion of insulin is increased, which in turn leads to hyperinsulinemia. Even the augmented insulin release is insufficient to inhibit the increase in blood glucose. However, since moxonidine-treated fructose-fed rats did not show any symptoms of hyperinsulinemia and exhibited glucose tolerances similar to untreated control rats, it follows that moxonidine effectively prevents or counteracts the insulin resistant state and inhibits the associated elevation of blood glucose levels. Moxonidine completely prevented the development of insulin resistance and hyperinsulinemia in fructose-fed rats.

Test 4

A double-blind placebo-controlled study of the effect of moxonidine administration on insulin resistance/glucose intolerance in obese patients with hypertension was carried out using the hyperinsulinemic euglycemic clamp technique.

Seventy-four patients, aged 28–74, were included in the study. Over a period of 8 weeks a group of 37 patients received 0.2 mg moxonidine twice daily and a control group of 37 patients received placebo twice daily. Fasting glucose levels and insulin sensitivity were measured before and after the 8 week treatment.

In order to quantitatively measure the insulin sensitivity, the effect of insulin in peripheral glucose uptake was determined by the euglycemic hyperinsulinemic clamp technique (see A. R. Starke, Determination of Insulin Sensitivity; Methodological Considerations, *J. Cardiovas. Pharmacol.*, 1992, 20 Suppl. 11:S17–S21). In this technique, by definition, the insulin concentration is fixed at a desired level, preferably within physiological ranges, by a constant insulin infusion and the glucose concentration is clamped (=kept constant) at the euglycemic level by a variable glucose infusion. The rate of glucose infusion necessary to maintain euglycemia is adjusted according to the frequent glucose determinations.

The insulin infusion rate in this study was fixed at 56 mU/m$^2$/min. A plasma glucose concentration of 5.1 mmole/l was targeted. The hyperinsulinemic stimulus (provided by the insulin infusion) was maintained for 120 min with steady state equilibrium achieved during the last 60 min. Blood samples were taken at 5 min intervals for glucose measurements at the bedside. The amount of glucose uptake (mg/kg/min) during the clamp was calculated for each 20 minute interval after the first 20 minutes. The mean rate of glucose uptake for the last 60 minutes was used as the M-value [mg/(kg·min)]. The insulin sensitivity index (M/I) [mg/(kg·min)] per mU/liter·100] was calculated by the amount of glucose taken up by the mean insulin concentration during the same period of time.

The results after 8 weeks of moxonidine treatment are shown in the following table:

|  | Moxonidine N = 37 | | Placebo N = 37 | |
|---|---|---|---|---|
|  | Before | After | Before | After |
| Fasting Plasma Glucose | 5.95 ± 0.88 | 5.82 ± 0.79* | 5.64 ± 0.76 | 5.66 ± 0.72 |
| M-value [mg/(kg · min)] | 3.58 ± 1.47 | 3.95 ± 1.55* | 4.24 ± 1.98 | 4.46 ± 2.02 |

|  | Moxonidine N = 37 | | Placebo N = 37 | |
| --- | --- | --- | --- | --- |
|  | Before | After | Before | After |
| Insulin sensitivity index [mg/(kg · min)] per mU/l · 100 | 3.56 ± 1.75 | 3.96 ± 2.25* | 4.39 ± 2.44 | 4.54 ± 2.49 |

Data are means ± SD; p-values (analysis of variance) for group comparisons of differences to baseline
*p < 0.05 for intragroup differences to baseline
**p < 0.01 for intragroup differences to baseline From the table it can be seen that in the moxonidine group, the values of fasting plasma glucose decreased in a statistically significant manner compared to baseline values (−0.13 mmole/liter, p<0.05). In the placebo group, the changes compared to baseline values were not significant (+0.01 mmole/liter, ns).

M-values in the moxonidine group increased in a statistically significant manner compared to baseline values (+0.37 mg/kg·min), p<0.05). The insulin sensitivity index (M/I) increased in a statistically significant manner compared to baseline values in the moxonidine group (+0.40 mg/(kg·min) per mU/liter·100, p<0.05), whereas values in the placebo group remained substantially unchanged.

This test data demonstrates that moxonidine treatment over 8 weeks in comparison to placebo improves insulin sensitivity, improves glucose uptake and decreases fasting plasma glucose in insulin resistant/glucose intolerant patients. The treatment effect in contrast to placebo is especially pronounced in patients having a low insulin sensitivity index (M/I<3.6).

The doses to be used may vary from individual to individual and of course vary according to the nature of the condition to be treated and the form of administration. In general, daily doses in the range from 0.2 to 0.8 mg, preferably 0.4 to 0.8 mg, are suitable for the treatment of hyperglycemic conditions in humans by oral administration.

The following example is intended to illustrate in further detail the production of a pharmaceutical preparation containing moxonidine which is suitable for the treatment of hyperglycemias without, however, restricting the scope of the application.

EXAMPLE 1

Moxonidine-containing Film-coated Tablets

| Composition: | |
| --- | --- |
| Tablet cores: | |
| Moxonidine | 0.020 parts |
| Lactose | 9.580 parts |
| Povidone USP | 0.070 parts |
| Crospovidone USP | 0.300 parts |
| Magnesium stearate | 0.030 parts |
| (water | 0.750 parts) |
| Total solid | 10.000 parts |
| Film coating: | |
| Hydroxypropylmethylcellulose | 0.156 parts |
| 30% aqueous ethylcellulose dispersion | 0.480 parts |
| (Δ solid) | (0.144) parts |
| Polyethylene glycol 6000 | 0.030 parts |
| Titanium dioxide | 0.150 parts |
| Talc | 0.1197 parts |
| Red iron oxide | 0.0003 parts |
| (Water | 3.864 parts) |
| Total solid | 0.600 parts |
| Total amount of film-coating suspension | 4.800 parts |

4.8 kg of the foregoing film-coating suspension were used to coat 10,000 tablet cores each weighing 100 mg.

Tablet Core Production:

The moxonidine and the lactose were mixed. The mixture was moistened with a solution of the binder povidone in water and thoroughly kneaded, and the resulting product was spread out on drying racks and dried at a temperature of about 50° C. to a moisture content of at most 0.5%. The dried product was passed through a 0.75 mm screen (Frewitt machine). After mixing the resulting granules with crospovidone and magnesium stearate, tablet cores having a weight of 100 mg were pressed therefrom such that each tablet core contained 0.2 mg of active compound.

Production of the Film-coating Suspension:

The hydroxypropylmethylcellulose and the polyethylene glycol 6000 were dissolved in one part of the water. A suspension of talc, titanium dioxide and iron oxide in the remaining water was added to this solution with stirring. The resulting suspension was diluted with the 30% strength aqueous ethylcellulose dispersion with gentle stirring.

Film-coating of the Tablet Cores

The film-coating suspension was sprayed onto the tablet cores in a film-coating apparatus, while warm air at about 70° C. warmed the tablet cores to a temperature of about 45° C. The film-coated tablets were then dried for 16 hours at a temperature of about 45° C.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of treating at least one glucose metabolism affecting condition selected from the group consisting of insulin resistance and glucose intolerance in a mammal, said method comprising administering to said mammal an effective glucose metabolism improving amount of 4-chloro-5-{(4,5-dihydro-1H-imidazol-2-yl) amino}-6-methoxy-2-methylpyrimidine of formula I

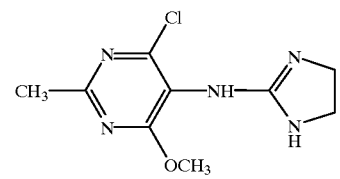

or a physiologically acceptable acid addition salt thereof.

2. A method according to claim 1, wherein said 4-chloro-5-[(4,5-dihydro-1H-imidazol-2-yl)amino]-6-methoxy-2-methylpyrimidine or salt thereof is incorporated into a dosage form selected from the group consisting of uncoated tablets, coated tablets, capsules, powders, granules, solutions, suspensions and emulsions and is administered orally.

3. A method according to claim 2, wherein said 4-chloro-5-[(4,5-dihydro-1H-imidazol-2-yl)amino]-6-methoxy-2-methylpyrimidine or salt thereof is administered at a dosage of from 0.2 to 0.8 mg per day.

4. A method according to claim 3, wherein said 4-chloro-5-[(4,5-dihydro-1H-imidazol-2-yl)amino]-6-methoxy-2-methylpyrimidine or salt thereof is administered at a dosage of from 0.4 to 0.8 mg per day.

5. A method according to claim 1, wherein said glucose metabolism disorder is insulin resistance.

6. A method according to claim 1, wherein said glucose metabolism disorder is glucose intolerance.

* * * * *